US012638418B2

(12) United States Patent
Cachelin et al.

(10) Patent No.: US 12,638,418 B2
(45) Date of Patent: May 26, 2026

(54) METHOD OF SENSING

(71) Applicant: Sumitomo Chemical Co., Ltd., Tokyo (JP)

(72) Inventors: Pascal Cachelin, Godmanchester (GB); Daniel Tobjork, Godmanchester (GB)

(73) Assignee: Sumitomo Chemical Co., Ltd., Tokyo (JP)

( * ) Notice: Subject to any disclaimer, the term of this patent is extended or adjusted under 35 U.S.C. 154(b) by 153 days.

(21) Appl. No.: 18/284,235

(22) PCT Filed: Mar. 30, 2022

(86) PCT No.: PCT/EP2022/058422
§ 371 (c)(1),
(2) Date: Sep. 26, 2023

(87) PCT Pub. No.: WO2022/207710
PCT Pub. Date: Oct. 6, 2022

(65) Prior Publication Data
US 2024/0167978 A1 May 23, 2024

(30) Foreign Application Priority Data
Mar. 31, 2021 (GB) ...................................... 2104647

(51) Int. Cl.
*G01N 27/416* (2006.01)
*G01N 33/00* (2006.01)

(52) U.S. Cl.
CPC ....... *G01N 27/416* (2013.01); *G01N 33/0027* (2013.01)

(58) Field of Classification Search
CPC ............. G01N 27/416; G01N 33/0014; G01N 33/0027; G01N 33/0047; G01N 33/0059
See application file for complete search history.

(56) References Cited

U.S. PATENT DOCUMENTS

2008/0093226 A1     4/2008   Briman et al.
2017/0038326 A1*   2/2017   Motayed ............ G01N 33/0047
2019/0323985 A1*   10/2019   Xiao .................. G01N 27/4045

OTHER PUBLICATIONS

E.C. Nallon, Discrimination Enhancement with Transient Feature Analoysis of a Graphene Chemical Sensor, Analytical Chemistry, 2016(88), pp. 1401-1406 (Year: 2016).*
(Continued)

*Primary Examiner* — C. Sun
(74) *Attorney, Agent, or Firm* — Wolf, Greenfield & Sacks, P.C.

(57) ABSTRACT
A method of sensing a target material in an environment is disclosed. The method comprises exposing a sensor to an environment for a first exposure period. The method further comprises, following the first exposure period, isolating the sensor from any target material in the environment for a first isolation period wherein the first isolation period is less than a characteristic recovery period for the sensor to return to a baseline after the first exposure period. The method further comprises, following the first isolation period, exposing the sensor to the environment for a second exposure period, and determining a concentration of the target material from a response of the sensor during the second exposure or a response of the sensor during the first and second exposure.

11 Claims, 9 Drawing Sheets

(56)            References Cited

OTHER PUBLICATIONS

International Search Report and Written Opinion dated Jul. 4, 2022, in connection with International Application No. PCT/EP2022/058422.

Combined Search and Examination Report dated Dec. 1, 2021, in connection with British Application No. GB2104647.9.

Nallon et al., Discrimination Enhancement with Transient Feature Analysis of a Graphene Chemical Sensor. Analytical Chemistry. Dec. 29, 2015;88(2):1401-1406.

* cited by examiner

METHOD OF SENSING

RELATED APPLICATIONS

This application is a national stage filing under 35 U.S.C. § 371 of International PCT Application PCT/EP2022/058422, filed Mar. 30, 2022, which claims priority to United Kingdom Application, GB 2104647.9, filed on Mar. 31, 2021, each of which is incorporated herein by reference.

BACKGROUND

It may be desirable to determine the presence and/or concentration of certain materials in an environment. However, a sensor used for this purpose may respond to one or more materials in the environment other than the target material. This situation can be referred to as cross-sensitivity.

Cross-sensitivity can occur when operating sensors in atmospheres that contain interfering agents (interferents). One approach to address cross-sensitivity is to remove interferents from an environment by filtration. However, it is not always possible to find a filter that removes interferents while letting through the target gas.

Ethylene produced by plants can accelerate ripening of climacteric fruit, the opening of flowers, and the shedding of plant leaves. It is therefore desirable to sense the presence, concentration or change in concentration of ethylene in an environment containing interferents such as other volatile organic compounds.

SUMMARY

According to a first aspect of the disclosure there is provided a method of sensing a target material in an environment. The method comprises exposing a sensor to an environment for a first exposure period. The method further comprises following the first exposure period, isolating the sensor from any target material in the environment for a first isolation period wherein the first isolation period is less than a characteristic recovery period for the sensor to return to a baseline after the first exposure period; The method further comprises following the first isolation period, exposing the sensor to the environment for a second exposure period. The method further comprises determining a concentration of the target material from a response of the sensor during the second exposure or a response of the sensor during the first and second exposure.

If the magnitude of response of the sensor to any target material in the environment is greater than the magnitude of response of the sensor to any interferent(s) in the environment and the rate of recovery of the sensor to any target material is faster than the rate of recovery of the sensor to the interferent(s) during the first isolation period, the concentration of the target material may be determined by measuring a change in response of the sensor during the second exposure period.

If the magnitude of response of the sensor to any target material is less than the magnitude of response of the sensor to any interferent(s) in the environment and the rate of recovery of the sensor to the target material is slower than the rate of recovery of the sensor to the interferent(s) during the first isolation period, the concentration of the target material may be determined by measuring the difference between a change in response of the sensor during the first exposure period and a change in response of the sensor during second exposure period.

The first isolation period may be the time taken for a response of the sensor to return to between 90% and 10% of a peak response of the sensor during the first exposure period after the start of the first isolation period.

The first isolation period may be the time taken for a response of the sensor to return to between 60% and 40% of a peak response of the sensor during the first exposure period after the start of the first isolation period.

Isolating the sensor from the target material in the environment may comprise filtering the target material from the environment before the sensor is exposed to the environment or may comprise exposing the sensor to an environment which does not contain the target material.

The method may further comprise isolating the sensor from at least one interferent(s) in the environment by filtering the at least one interferent(s) from the environment before the sensor is exposed to the environment or by exposing the sensor to an environment which does not contain the at least one interferent(s).

The method may further comprise at least n isolation periods and n+1 exposure periods and wherein n is at least 2.

The target material may be ethylene.

The environment may contain one or more volatile organic compounds, not including the target material.

The sensor may be a gas sensor, for example, an electrochemical gas sensor.

According to a second aspect of the disclosure there is provided a computer program which, when executed by at least one processor, causes the at least one processor to perform the method of the first aspect of the disclosure.

According to a third aspect of the disclosure there is provided a computer program product comprising a computer-readable medium, which stores the computer program according to the second aspect of the disclosure.

According to a fourth aspect of the disclosure there is provided an apparatus comprising at least one processor and memory in operative communication with the at least one processor. The at least one processor configured to perform the method of the first aspect of the disclosure.

The present inventors have surprisingly found that by using the inherent kinetic differences in how the sensor responds to different agents, a response of the sensor to the target material can be distinguished from a response of the sensor to interferents without the need, for example, additional sensors to differentiate the target material from the interferents and/or filters to remove any interferents. Therefore, sensing of a target material in an environment containing interferents may be performed using simple and low-cost apparatus.

BRIEF DESCRIPTION OF THE DRAWINGS

The disclosed technology and accompanying figures describe some implementations of the disclosed technology.

Figure 1:
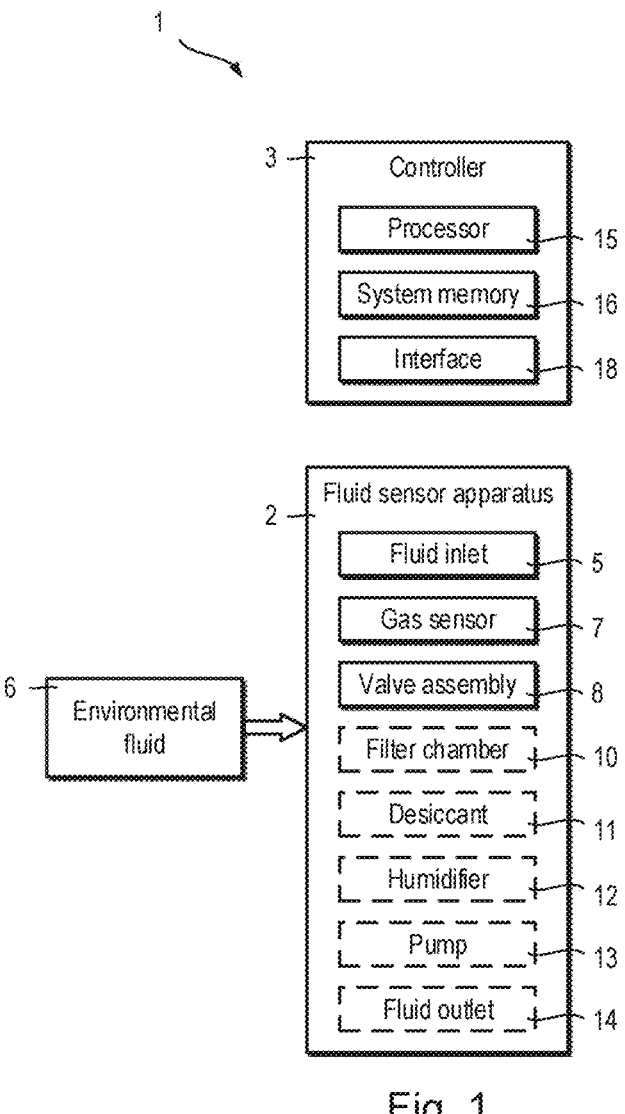
FIG. 1 is a system block diagram for determining the presence, concentration or change in concentration of a target material in an environment.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology. Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. The machine-readable medium includes non-transitory medium, where non-transitory excludes propagation signals. For example, a processor can be connected to a non-transitory computer-readable medium that stores instructions for executing instructions by the processor.

It can often be desirable to sense a target material (e.g. an analyte) in an environment that contains other materials. These other materials can act as interfering agents (also referred to as "interferents") to sensors used to determine the presence, concentration or change in concentration of a target material. Such a situation can be referred to as cross-sensitivity. Cross-sensitivity can make the accuracy of the readings of the presence, concentration or change in concentration of a target material inaccurate. One approach to address cross-sensitivity is to filter the environment by removing interferents before exposing the filtered to a sensor to gain an accurate reading of a target material. An environment may contain zero, one or more than one interferent.

The present inventors have surprisingly found that by using the inherent kinetic differences in how the sensor responds to different agents, a response of the sensor to a target material, if present, can be distinguished from a response of the sensor to interferents without the need, for example, additional sensors to differentiate the target material from the interferents and/or filters to remove any interferents. Therefore, sensing of a target material in an environment containing interferents may be performed using simple and low-cost apparatus.

System Overview

Referring to FIG. 1, a sensor system 1 according to some embodiments for sensing the presence, concentration or change in concentration of a target material, if present, in an environment, for example a gaseous or liquid environment, is shown. The system 1 includes a sensor apparatus 2 operatively connected to a controller 3. The sensor apparatus 2 includes a fluid inlet 5 for entry of environmental fluid 6 into the apparatus; a sensor 6; and a valve arrangement 8 for controlling the flow of fluid through the apparatus 2. The vale arrangement 8 may be a single valve or a combination of valves for directing the flow of a fluid through the sensor apparatus 2. The sensor 7 is configured to respond to a target material in the environment. The target material may be a gas, a liquid, or a particulate in suspension in a fluid. The target material may be, for example, an alkene, e.g. i-methylcyclopropene or ethylene, preferably ethylene.

Optionally the sensor apparatus 2 may include one or more filter chambers 10, which may include, for example, a filter material. The filter may be a filter material, a filter mesh, a chemical filter, a scrubber, a getter or a filter device and the like. Optionally, if the fluid is a gas, the sensor apparatus 2 may further include a desiccant 11, and/or a humidifier (e.g. a water reservoir) 12. The sensor apparatus may further include a pump 13 for pumping fluid through the apparatus 2 and a fluid outlet 14 for returning the fluid to the environment. The of filter chambers comprising one of a filter material, a desiccant or a humidifier may be arranged in any suitable order before the fluid encounters the sensor 7.

The controller 3 may further include a processor 15, system memory 16, and an interface 18 (e.g. a display) to allow the controller 3 to be programmed, for example, by a human. The controller may include additional peripheral devices for recording environmental conditions, for example, a thermometer (not shown) and a hygrometer (not shown) and the like. In some embodiments, the controller 3 may be remote, that is away from the sensor apparatus 2, for example, the controller 3 and the sensor apparatus may be at different network locations. In some embodiments, the processor 15, the system memory 16 or the interface 18 may be at different network locations to the controller 3 and/or the sensor apparatus 2.

A "valve" as used herein means any apparatus configured to allow or block fluid flow through the valve and may be manually operable (e.g. by way of a manually operable tap) and/or may be electromechanical, e.g. a solenoid valve, controllable by a controller 3, e.g. a programmable controller. For example the controller 3 may control the valve arrangement 8 configuration. The controller 3 may be programmable via the interface 18.

The sensor apparatus 2 may be in wired or wireless communication with a controller 3 configured to receive measurements from the sensor 7. The controller 3 may include a processor 15 which may be configured to determine the presence, concentration and/or change in concentration of the target material from the received sensor measurements. The controller 3 may include system memory 16 which may store sensor measurements, and/or other environmental information recorded by the system 1. The controller 3 may be in wireless communication with the cloud (not shown) and send and receive data to the cloud. The processor 15 may perform calculations based on the sensor measurements and other environmental information recorded by the system 1. The processor 15 may be on the cloud and the calculations may be performed on the cloud. The sensor measurements and other environmental information may also be stored in memory 16 on the cloud. The interface 18 may be on the cloud, or there may be a second interface 18 on the cloud which a user can use to monitor and input the system 1. The first interface 18 on the controller 3 may be an interface between the controller 3 and the fluid sensor apparatus 2.

Sensor Types

A particular sensor 7 may exhibit different responses to different materials in a fluid environment 6. For example, the response of a particular sensor to a target material may differ from its response to one or more interferent materials in one or more of: speed of response upon exposure to the material; magnitude of response upon exposure to the material; and rate of recovery after exposure to the material to a baseline following exposure to the material. In some embodiments, the sensor 7 response to a target material, e.g. ethylene may be faster, of greater magnitude and/or of faster recovery than the corresponding response to an interferent. In some embodiments, the sensor 7 response to an interferent may be faster, of greater magnitude and/or of faster recovery than the corresponding response to a target material.

The sensor 7 may be any suitable sensor type. Suitable sensor types may be sensors where the sensor element directly interacts with the molecule. For example, electrochemical sensors, metal oxide sensors, surface acoustic wave sensors, field effect transistors (including organic field effect transistors (OFET)) or a quartz crystal microbalances.

Sensor Apparatus

Figure 2:
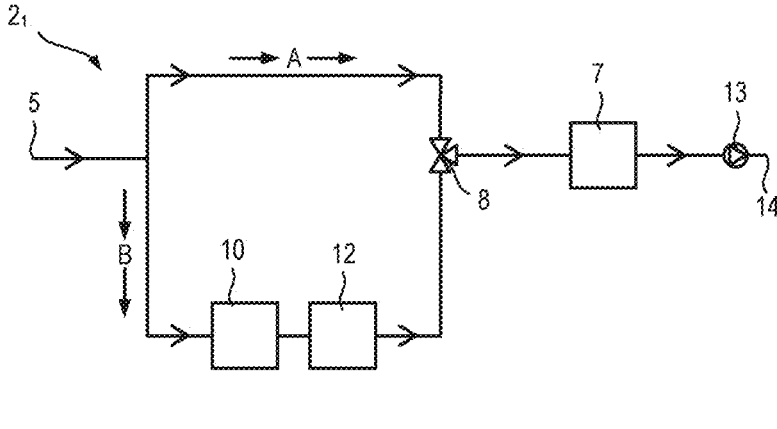
FIG. 2 is a first sensor apparatus according to some embodiments.

Referring to FIG. 2, a first sensor apparatus $2_1$ for determining a presence, a concentration or a change in concentration of a target material in an environment according to some embodiments of the present disclosure includes a fluid inlet 5 in fluid communication with an environment, a sensor 7 configured to sense a target material in the environment, and a valve arrangement 8 having a first and a second configuration (also referred to as 'exposed configuration' or 'isolated configuration' respectively, or simply 'exposed' or 'isolated') arranged between the sensor 7 and the inlet 5.

When the first sensor apparatus 21 is in the exposed configuration, the fluid environment 6 flows along the flow path 'A' and reaches the sensor 7 without being filtered. When the valve arrangement 8 is in the isolated configuration, the fluid environment 6 flows along the flow path 'B'. When fluid flows along flow path 'B', if present, any target material in the environment is removed from the environment before the fluid environment 6 reaches the sensor 7. The target material may be removed from the environment by a filter 10. One or more interferents may also be removed from the fluid environment by the same or different filters 10. If the fluid in the environment 6 is a gas, the first sensor apparatus $2_1$ may further include a filter chamber 10 comprising filter material, a desiccant (not shown), and/or a humidifier 12. The filter chamber 10, desiccant and humidifier 12 may be arranged in flow path 'B' between the inlet 5 and the sensor 7. The desiccant may be arranged in the filter chamber 10. The first sensor apparatus may further include a pump 13 for drawing fluid from the environment through the inlet 5 and past the filter 7, and an outlet for passing the fluid back into the environment after it has passed over the sensor 7.

In some embodiments, the valve arrangement 8 may be a two-way valve or a three-way valve.

Figure 3:
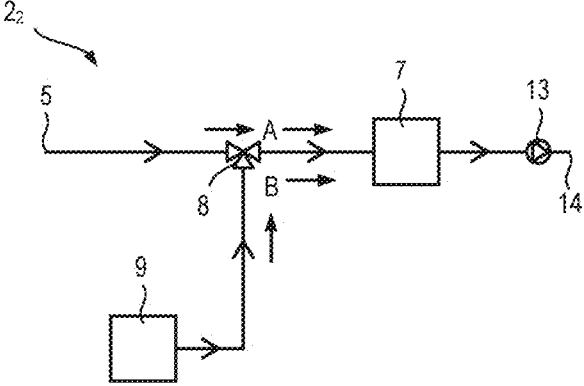
FIG. 3 is a second sensor apparatus according to some embodiments.

Referring also to FIG. 3, the second sensor apparatus $2_2$ is similar to the first sensor apparatus $2_1$. When the valve arrangement 8 is in the first configuration, the flow path marked 'A', the sensor 7 is in fluid communication with the fluid inlet 5. When the valve arrangement 8 is in the second configuration, the flow path marked 'B', the sensor 7 is not in fluid communication with the inlet 5 and is isolated from the environment. When the valve arrangement 8 is in the second configuration, there is fluid source 9 which does not contain the target material which is passed over the sensor 7. As fluid from the fluid source 9 passes over the sensor 7, the sensor 7 may recover from the exposure to the target material. The second sensor apparatus 2₂ may have one or more pumps 13 and outlets 14. In some embodiments, the flow paths path 'A' and path 'B' may join again after passing the sensor and a single pump may be used to draw fluid through the apparatus 2. In some embodiments, the valve arrangement 8 may be, for example, a two-way valve, a three-way valve, or a combination of two-way and/or three-way valves.

The first and second sensor apparatus 2₁, 2₂ may be cycled between the first and second configuration.

Sensor Responses

For a given sensor 7, the magnitude of the sensor's 7 response to a target material $m_t$ and to an interferent(s) $m_i$ will be known through calibration in advance of performing the method. The magnitude is defined as the expected size of a response in a likely operating scenario. Likewise, for a given sensor 7, the recovery rate of a sensor to a target material $r_t$ and to an interferent(s) $r_i$ after exposure will be known in advance of performing the method. In addition, for a given sensor, the speed of the sensor response to a target material $s_t$ and to an interferent(s) $s_i$ may also be known.

As will be explained in more detail later, knowing the relative magnitude of response, relative recovery rate and optionally relative speed of response between the target material and the interferent(s) allows the determination of the concentration of the target material in the environment. For example, knowing that the magnitude of the response to the target material $m_t$ is greater than the magnitude of response to the interferent(s) $m_i$ and that the recovery rate of a sensor to a target material $r_t$ is faster than the recovery rate to a an interferent(s) $r_i$ after exposure, it is possible to determine the concentration of the target material in the environment.

The magnitude of response to target and interferents $m_t$, $m_i$ can be calculated using the following equation:

$$\text{sensitivity (nA/ppm)} \times \text{actual concentration (ppm)} = \text{magnitude (nA)} \qquad (1)$$

The magnitudes of responses, the recovery rates and optionally, the speed of response will depend on the sensor type, the sensitivity of the sensor and the target material(s) and interferent(s) the sensor is exposed to. The magnitude of response to the target material $m_t$ may be, for example, more than 1.5 times, more than 2 times, more than 3 times or more than 4 times the magnitude of response to the interferent $m_i$. The recovery rate $r_t$ of the sensor to between 90% and 10% of the peak response after exposure to a target material, may be twice or three times or more than three times the recovery rate of the sensor after exposure to an intereferent(s) $r_i$ to between 90% and 10% of the peak response. For example, the recovery rate of a sensor to 70% of the peak response after exposure to a target material may be around 10 minutes or may be around 30 minutes, and the recovery rate of the sensor to 70% of the peak response after exposure to an interferent(s) may be around 20 minutes, or may be around 60 minutes. In another example, the recovery rate of a sensor to 20% of the peak response after exposure to a target material may be around 20 minutes, or may be around 60 minutes, and the recovery rate of the sensor to 20% of the peak response after exposure to an interferent(s) may be around 120 minutes.

Sensor Measurements

Figure 4:
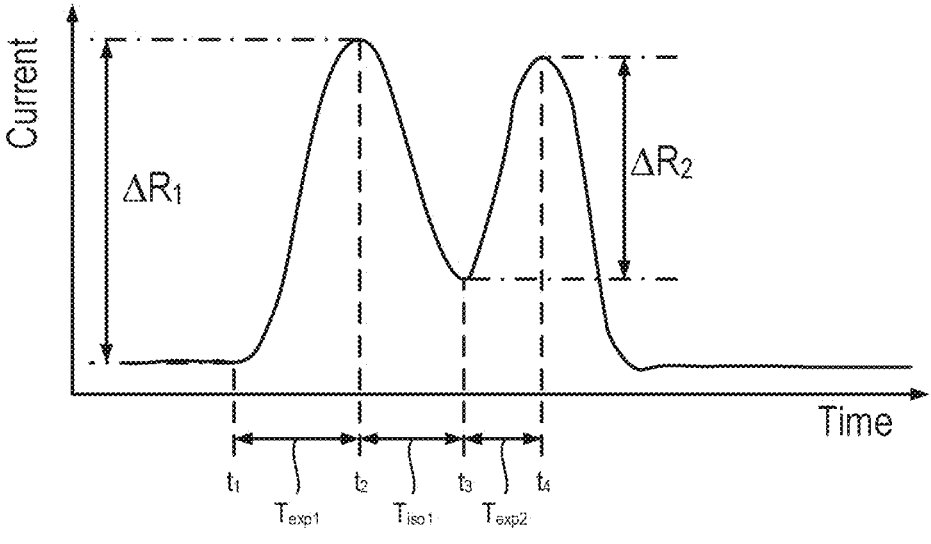
FIG. 4 illustrates current over time of a fluid sensor.

Referring to FIG. 4, a voltage is applied to a sensor 7 and the current measured from the sensor 7 over time as it is exposed or isolated from an environment containing a target material. At a first time point $t_1$ the sensor 7 is exposed to the environment for a first exposure period $T_{exp1}$. The response $\Delta R_1$ (e.g. change in current $\Delta I_1$) is measured and recorded. The measurement may be stored in the memory 16 of the controller 3. At a second time point $t_2$ the sensor 7 is isolated from the target material in the environment for a first isolation period $T_{iso1}$. The rate of recovery of the sensor 7 may be measured and recorded for the first isolation period $T_{iso1}$. The first isolation period $T_{iso1}$ ends at a third time point $t_3$ when the sensor 7 has recovered, but before the current reading of the sensor 7 has returned to the baseline, for example, the current reading from the sensor 7 may be between 90% and 10% of the sensor's 7 peak. This recovery time will depend on the sensor type, the sensitivity of the sensor and the target material(s) and interferent(s) the sensor is exposed to. At the third time point $t_3$, the sensor 7 is exposed to the environment for a second exposure period $T_{exp2}$ until a fourth time point $t_4$. The response $\Delta R_2$ (e.g. change in current $\Delta I_2$) from the sensor 7 during the second exposure period $T_{exp2}$ is measured and recorded.

The third time point $t_3$, that is, the start of the second exposure period $T_{exp2}$, may occur when the response recorded from the sensor 7 is between 90% and 10% or between 60% and 40% of the peak of the response during the first (or previous) exposure period $T_{exp1}$.

Other types of fluid sensors 7 may be used, and the change in response of other types of sensors 7 may be measured in different ways, for example, the response $\Delta R_1$, $\Delta R_2$ may be a change in voltage, a change in current, a change of resistance or a change in impedance (for example, for surface acoustic wave sensors (SAWS) or Quartz Crystal Microbalance (QCM) sensors) of the sensor 7.

Method of Determining Concentration

Figure 5:
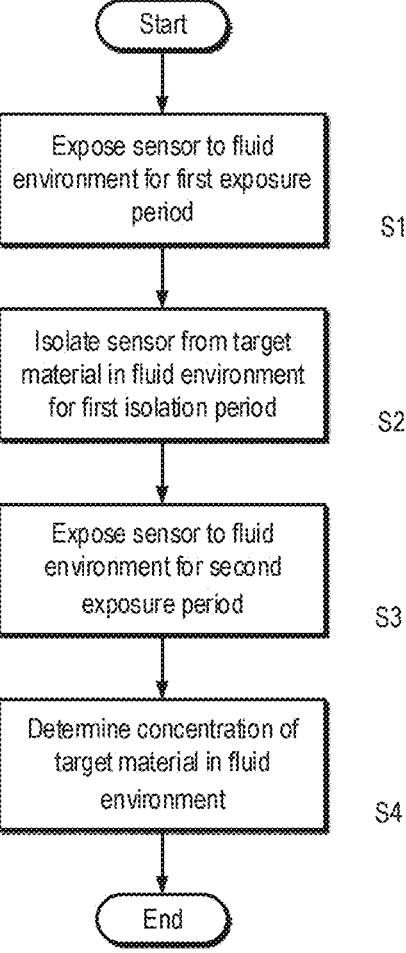
FIG. 5 is a process flow diagram according to some embodiments for determining the presence, concentration or change in concentration of a target material in an environment using measurements of a sensor apparatus.

Referring to FIG. 5, to determine the concentration of a target material, if present, in an environment may also contain interferents, a sensor 7 is exposed to a fluid environment, for example, a gaseous environment (step S1) for a first exposure period $T_{exp1}$. The fluid environment may include a target material and one or more interferents. The response during the first exposure $\Delta R_1$ of the sensor to the fluid environment is measured and recorded, for example, in the system memory 16. The type of sensor used will determine the type of measurement taken, for example the measurement may be a change in current or may be a change in voltage.

For example, in a gaseous environment containing ethylene as a target material to be sensed and volatile organic compounds as interferents, it will be known that a given sensor 7 responds with a greater magnitude and recovers more quickly in response to exposure to ethylene than to the volatile organic compounds. It may also be known that the sensor 7 responds more quickly to ethylene than to the volatile organic compounds.

Once the first exposure period $T_{exp1}$ has lapsed, the sensor 7 is isolated from any target material in the gaseous environment for a first isolation period $T_{iso1}$ (step S2). The sensor 7 may be isolated from any target material present in any suitable way, for example, any target material in the environment may be filtered to remove the target material, or the sensor 7 may be exposed to a non-environmental fluid which does not contain any target material. In previous fluid sensing methods an isolation period such as this would be used to return the sensor 7 reading to a baseline that indicated no presence of either target material or interferents. However, this method relies on the first isolation period $T_{iso1}$ being less than the period required for the sensor 7 to return to a baseline reading. Once the first isolation period $T_{iso1}$ has lapsed, the sensor 7 is exposed to the fluid environment for a second exposure period $T_{exp2}$ (step S3). The response during the second exposure $\Delta R_2$ of the sensor to the fluid environment is measured and recorded, for example, in the system memory 16.

Likewise, the sensor 7 may be isolated from any interferent(s) present in any suitable way, for example, any interferent(s) present in the environment may be filtered to remove the interferent(s), or the sensor 7 may be exposed to a non-environmental fluid which does not contain any, or a particular, interferent(s).

Using the responses during the first and second exposures $\Delta R_1$, $\Delta R_2$ the concentration of the target material is determined (step S4). For example, in a first scenario, if the magnitude of the response to a target material $m_t$ is greater than the magnitude of response to an interferent $m_i$ and the nitrogen source 22, an ethylene source 23 and a volatile organic compound source 24. The apparatus 20 further includes first, second and third mass flow controllers 25, 26, 27 each connected to one of the air source 21, the nitrogen source 22 and the ethylene source 23 to control the flow of each source into the sensor apparatus 20. The apparatus 20 further includes a sensor 28 and an outlet 29 for expelling the gas out of the apparatus, and a valve apparatus 3o for controlling the presence or absence of the volatile source 24 in the sample provided to the sensor 28. The third sensor apparatus may include a second valve arrangement to control the fluid communication between the volatile organic compound source 24 and the sensor 28. In some embodiments, the second valve arrangement is not needed because the flow path between the volatile organic compound source 24 and the sensor 28 is of sufficient length that the diffusion path is too long for a detectable level of volatile diffusion to happen.

Referring to Table 1, four conditions of exposing an electrochemical gas sensor to an environment containing either volatile organic compounds (VOCs), ethylene and VOCs or just Ethylene for different periods of exposure and recovery.

TABLE 1

| Condition | Sample | Duration of exposure (minutes) | Number of consecutive exposures | Recovery time (minutes) |
|---|---|---|---|---|
| C1 | Volatile organic compounds (VOCs) | 5 | 3 | 25 |
| C2 | Ethylene + VOCs | 5 | 2 | 25 |
| C3 | Ethylene + VOCs | 5 | 5 | 10 |
| C4 | Ethylene | 5 | 3 | 25 | recovery rate to a target material $r_t$ is greater than the recovery rate to an interferent $r_i$, then the concentration of the target material is proportional to response during the second exposure $\Delta R_2$. In a second scenario, if the magnitude of the response to an interferent $m_i$ is greater than the magnitude of the response to the target material $m_t$, and the recovery rate to an interferent $r_i$ is greater than the recovery rate to the target material $r_t$, then the concentration of the target material is proportional to the response during the first exposure $\Delta R_1$ minus the response during the second exposure $\Delta R_2$. In a third scenario where the recovery rate to an interferent $r_i$ is greater than the recovery rate to the target material $r_t$, and the magnitude of the response to a target material $m_t$ and to an interferent $m_i$ are approximately equal, then the rate of response and the rate of recovery of the sensor 7 can be used to determine the concentration of the target material. A particular sensor 7 may be calibrated before use so that the responses and the kinetics of the sensor to a target material and responses to one or more interferents present. Such a calibration may allow more accurate concentrations of a target material to be derived.

The sensor 7 can be exposed more than once, allowing a plurality of sensor responses to be measured. Using more than one response or more than one pair of responses can increase the accuracy of the target material concentration measurement.

Any one of the steps S1 to S4 may be performed by a computer, and instructions to perform each step may be stored on computer-readable media.

Experiments

Figure 6:
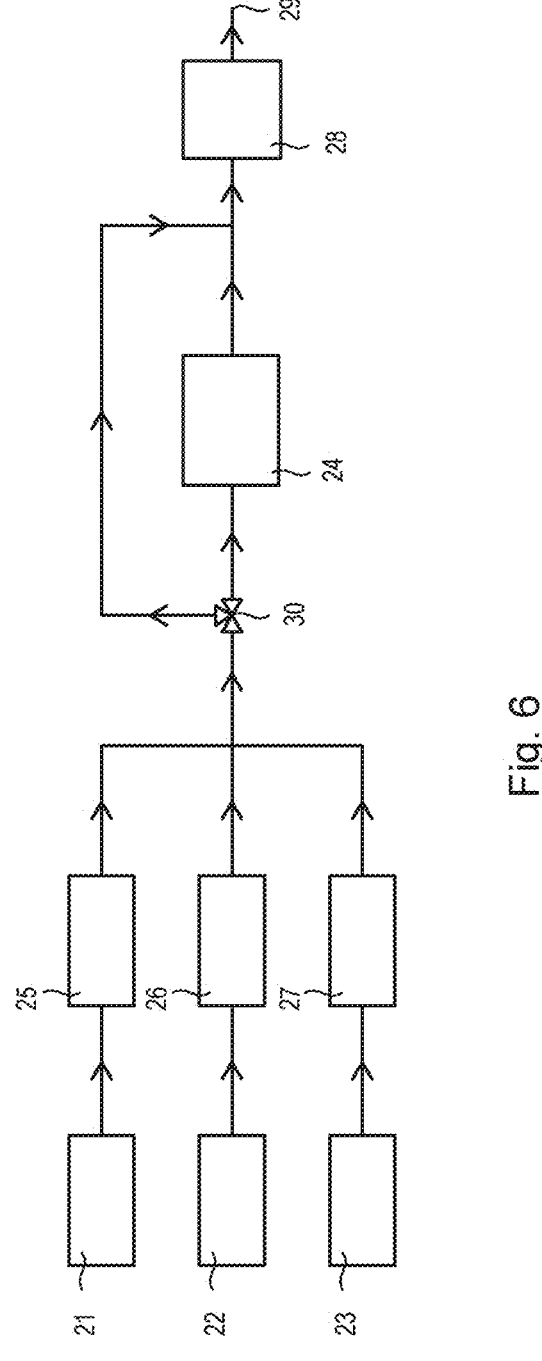
FIG. 6 illustrates third sensor apparatus.

Referring to FIG. 6, a third gas sensor apparatus 20 used for calibration of a sensor 7 includes an air source 21, a A Membrapor S200 electrochemical ethylene sensor was exposed to either 10 ppm of ethylene gas (C4) or 100 ppm of mixed volatiles (C1) (including butyl acetate, ethyl acetate and isopropanol) or both ethylene and mixed volatiles (C2 and C3). Exposures were controlled precisely using mass flow controllers (MFCs), programmed to dilute more highly concentrated samples of the volatile compounds to the required concentration. Voltages values were monitored, and peak prominence determined using the SciPy 'find_peaks' package in Python.

Figure 7:
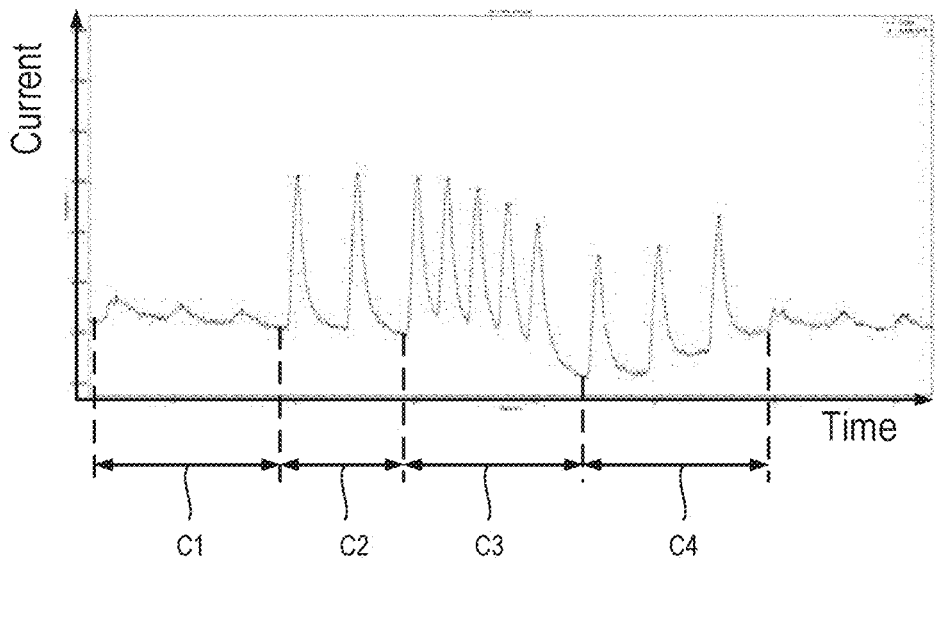
FIG. 7 illustrates current of a fluid sensor over time.

Referring to FIG. 7, the response shown in current of an electrochemical gas sensor to conditions C1 to C4 over time is shown. The rate of recovery of the electrochemical gas sensor in condition C1 was slower to recover from an exposure than a sample consisting of just ethylene.

Figure 8:
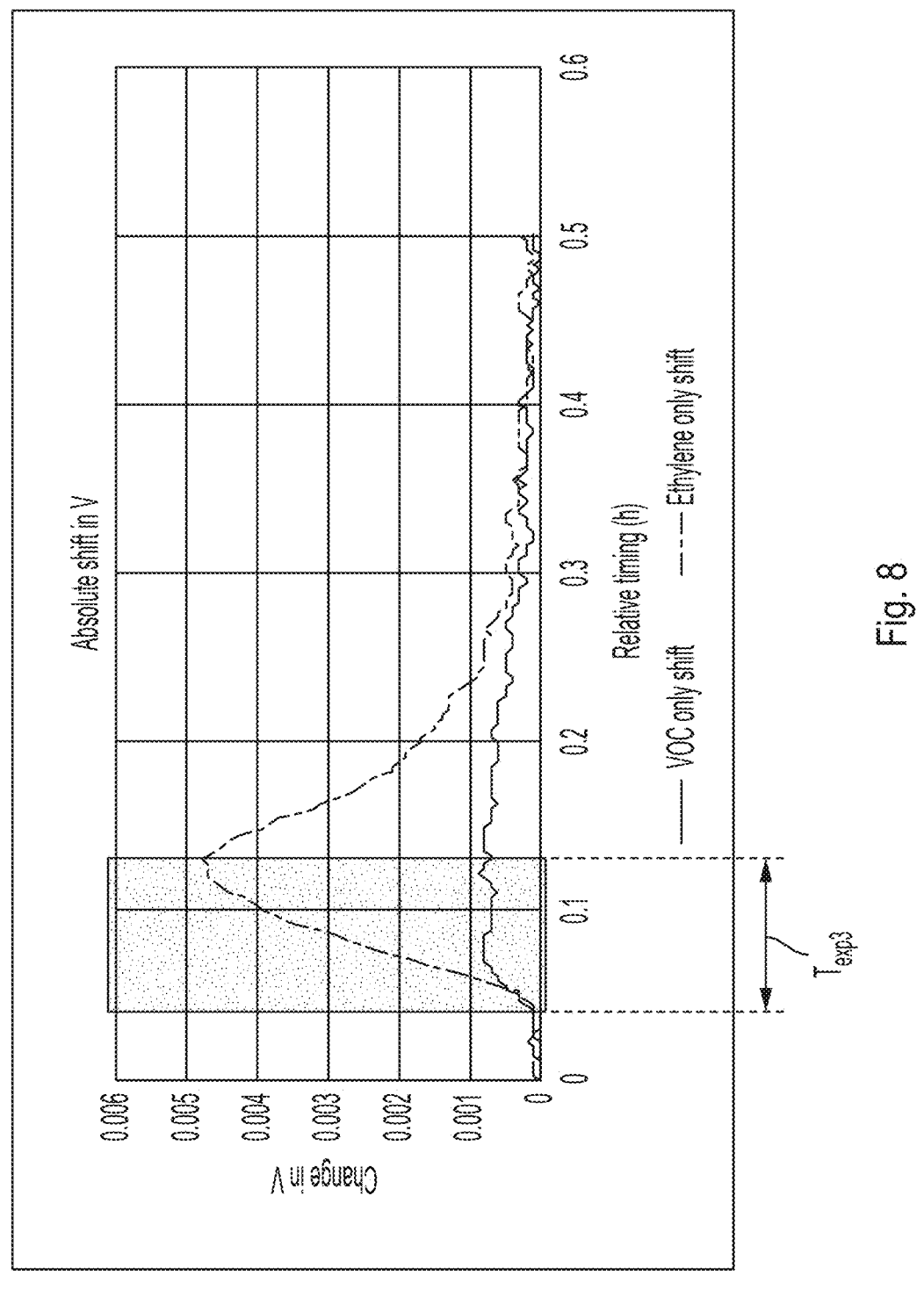
FIG. 8 illustrates change in voltage over time.
Figure 9:
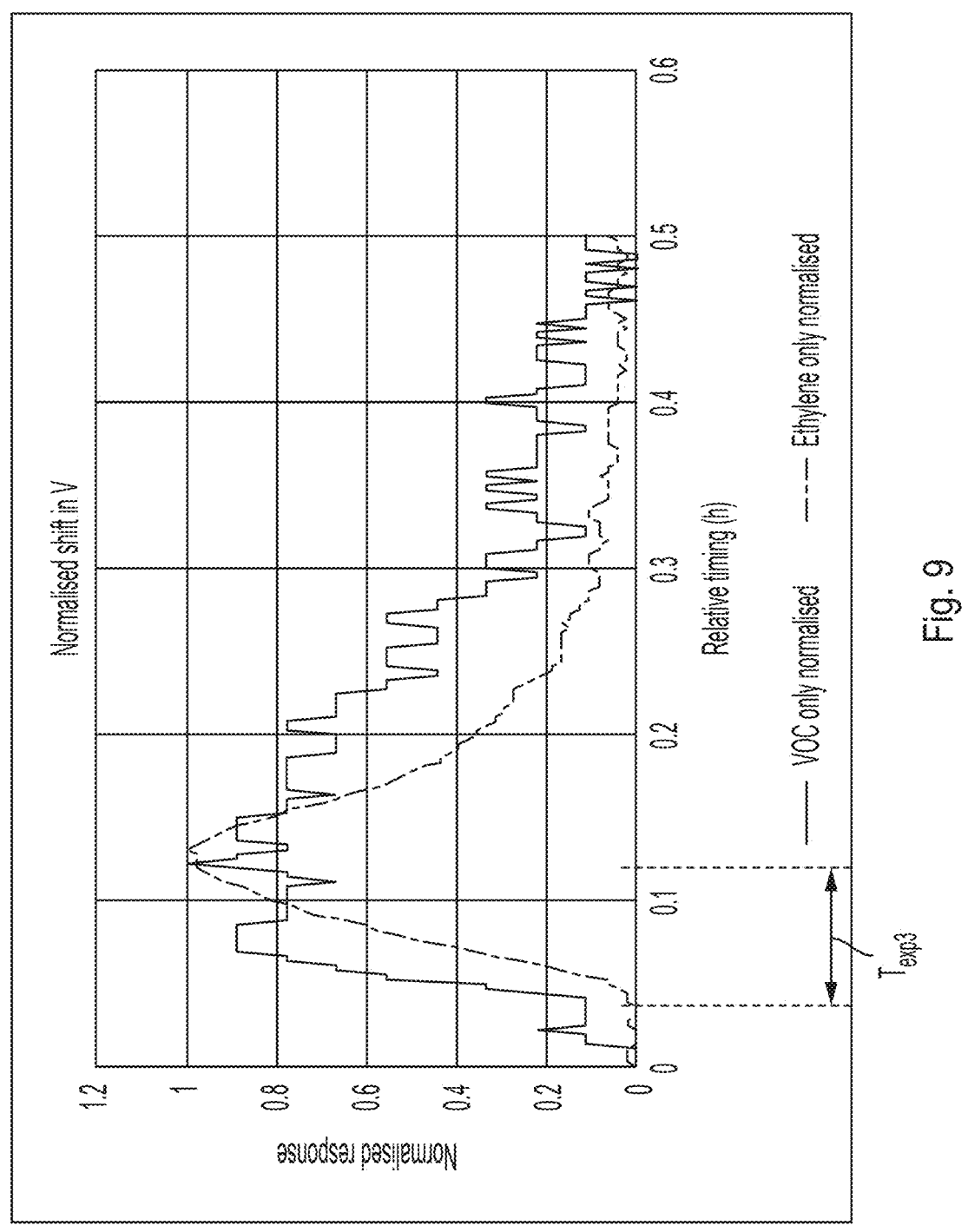
FIG. 9 illustrates a normalised graph of the data in FIG. 8.

Referring also to FIGS. 8 and 9, the differences recovery of the electrochemical gas sensor when exposed to both ethylene and VOCs can be seen more clearly when plotted together. FIG. 8 shows the normalised data from FIG. 8.

This difference in the kinetics of the interaction between the ethylene and VOCs can be used to increase the accuracy of the sensor 7 readings. Such an approach is the basis of time-resolved laser spectroscopy. In this, a single molecule is moved into an excited state by application of a pulse of energy from a laser. By maintaining the molecule in this excited state through the application of frequent, rapid addition laser pulses, it is possible to study the dynamics of the excited state without the result being masked by the additional slower process of relaxation into the ground state. By performing a series of exposures with shorter recovery times (condition C3 in Table 1), it is possible to replicate this effect, using the initial exposure to move the sensor into a state analogous to an "excited state", and then performing subsequent exposures at frequent intervals to separate the dynamic processes of the target material (analyte) and interferent absorption and desorption.

Figure 10:
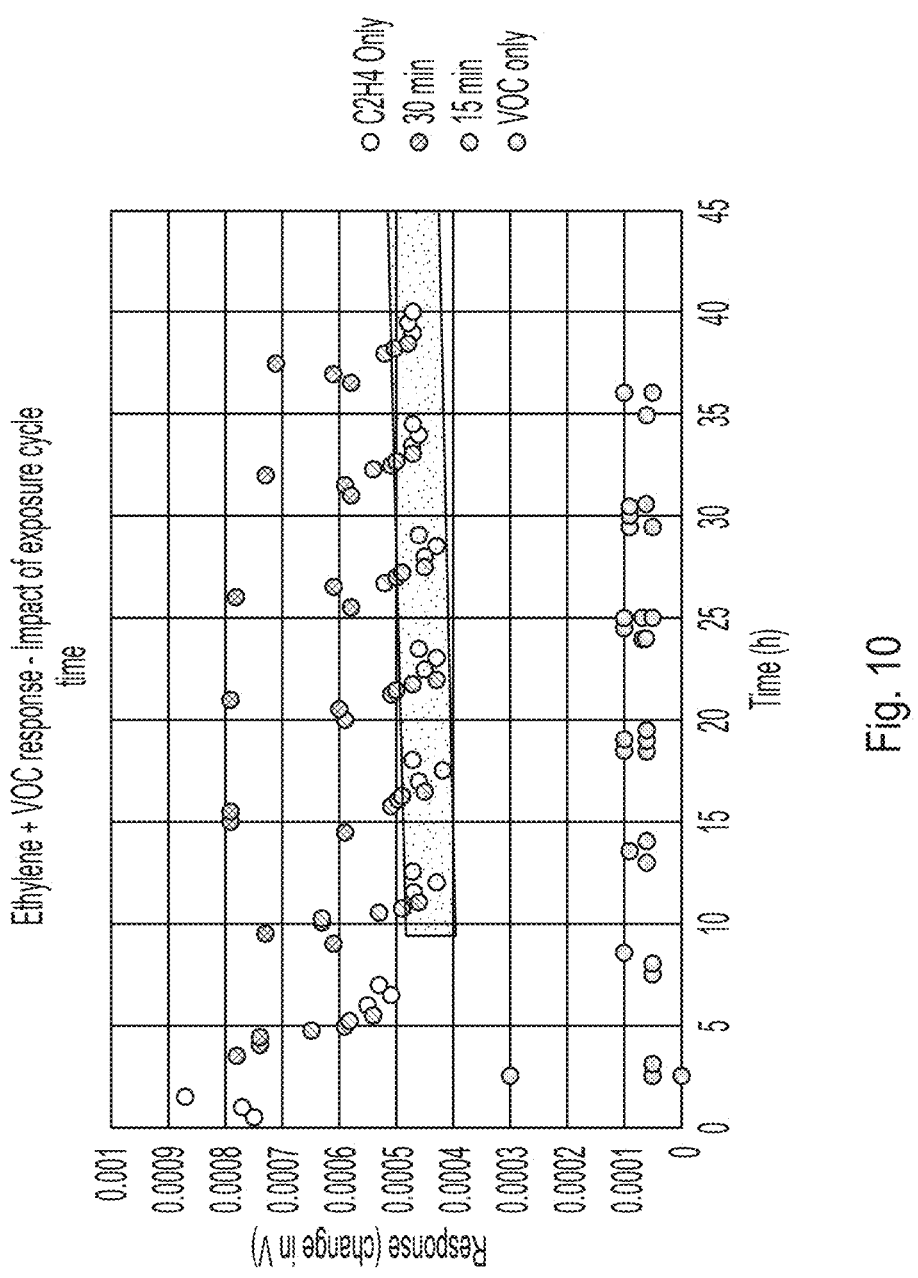
FIG. 10 illustrates change in voltage over time for four experimental conditions.

Referring to FIG. 10, by using the different kinetic responses to the target material and the interferent(s), it is possible to gain a greater accuracy of the sensor reading. The response of a sensor 7 as determined by magnitude of peak against time for the condition C1 to C4 as outlined in Table 1 are shown. The shaded area indicates a response of within approximately 10% of the response to ethylene only. It can be seen that the condition with the shortest recovery time, C3, provides responses which are closest to that where ethylene alone is present.

As demonstrated above, while performing a single response results in significantly impacted sensor readings, performing multiple exposures with shorter recovery times significantly increases accuracy. Furthermore, as can be seen in FIG. 10, the accuracy of this measurement increases with subsequent pulses. This can be attributed to a better separation of the two dynamic processes.

The invention claimed is:

1. A method of sensing a target gas in an environment comprising:

exposing an electrochemical gas sensor to the environment for a first exposure period, wherein the sensor has:
a known magnitude of response to the target gas upon exposure to the target gas for the first exposure period;
a known magnitude of response to one or more interferents upon exposure to the one or more interferents for the first exposure period;
a known rate of recovery after exposure to the target gas following the first exposure period; and
a known rate of recovery after exposure to the one or more interferents following the first exposure period;
following the first exposure period, isolating the electrochemical gas sensor from any of the target gas in the environment for a first isolation period wherein the first isolation period is less than a characteristic recovery period for the electrochemical gas sensor to return to a baseline after the first exposure period and is a period in which the electrochemical gas sensor response returns to between 90% and 10% of a peak response after exposure to the target gas;
following the first isolation period, exposing the electrochemical gas sensor to the environment for a second exposure period; and
determining a concentration of the target gas from a response of the electrochemical gas sensor during the second exposure period or a response of the sensor during the first and second exposure periods,
wherein the magnitude of response of the electrochemical gas sensor to any of the target gas in the environment is greater than the magnitude of response of the electrochemical gas sensor to any of the one or more interferents in the environment and the rate of recovery of the electrochemical gas sensor to any of the target gas is faster than the rate of recovery of the electrochemical gas sensor to the one or more interferents during the first isolation period, and wherein the concentration of the target gas is determined by measuring a change in response of the electrochemical gas sensor during the second exposure period.

2. A method according to claim 1 wherein if the magnitude of response of the electrochemical gas sensor to any of the target gas is less than the magnitude of response of the electrochemical gas sensor to any of the one or more interferents in the environment and the rate of recovery of the electrochemical gas sensor to the target gas is slower than the rate of recovery of the electrochemical gas sensor to the one or more interferents during the first isolation period, the concentration of the target gas is determined by measuring the difference between a change in response of the electrochemical gas sensor during the first exposure period and a change in response of the electrochemical gas sensor during second exposure period.

3. A method according to claim 1 wherein the first isolation period is the time taken for a response of the electrochemical gas sensor to return to between 90% and 10% of the peak response of the electrochemical gas sensor during the first exposure period after the start of the first isolation period.

4. A method according to claim 1 wherein isolating the electrochemical gas sensor from any of the target gas in the environment comprises filtering the target gas from the environment and exposing the electrochemical gas sensor to the filtered environment or comprises exposing the electrochemical gas sensor to a gas which does not contain the target gas.

5. A method according to claim 1 wherein the method further comprises isolating the electrochemical gas sensor from any of the one or more interferents in the environment by filtering any of the one or more interferents from the environment before the electrochemical gas sensor is exposed to the environment or comprises exposing the electrochemical gas sensor to a gas which does not contain any of the one or more interferents.

6. A method according to claim 1 comprising at least n isolation periods and n+1 exposure periods and wherein n is at least 2.

7. A method according to claim 1 wherein the target gas is ethylene.

8. A method according to claim 1 wherein the environment contains one or more volatile organic compounds, in addition to the target gas.

9. A computer program which, when executed by at least one processor, causes the at least one processor to perform the method of claim 1.

10. A computer program product comprising a computer-readable medium, which stores the computer program according to claim 9.

11. Apparatus comprising:
at least one processor; and
memory in operative communication with the at least one processor;
the at least one processor configured to perform the method of claim 1.

* * * * *